United States Patent [19]

Isnard

[11] Patent Number: 5,427,776
[45] Date of Patent: Jun. 27, 1995

[54] ALOE WATER PREPARATION

[76] Inventor: Camille Isnard, B.P. 4159, Noumea (Nouvelle Calédonie), France

[21] Appl. No.: 262,536

[22] Filed: Jun. 20, 1994

Related U.S. Application Data

[63] Continuation of Ser. No. 601,108, Oct. 22, 1990, abandoned.

[30] Foreign Application Priority Data

Oct. 23, 1989 [FR] France ................. 89 13832

[51] Int. Cl.⁶ .................. A61K 7/06; A61K 9/10
[52] U.S. Cl. ............... 424/70.1; 424/195.1; 424/74; 514/880; 514/937; 514/944; 132/202
[58] Field of Search ............ 424/70, 195.1, 70.1, 424/74; 514/880, 944, 937; 132/202

[56] References Cited

U.S. PATENT DOCUMENTS

| | | | |
|---|---|---|---|
| 4,500,511 | 2/1985 | Kigasawa et al. | 424/70.1 |
| 4,656,029 | 4/1987 | Grollier et al. | 424/70.1 |
| 4,917,890 | 4/1990 | McAnalley | 424/195.1 |
| 4,994,265 | 2/1991 | White | 424/74 |

FOREIGN PATENT DOCUMENTS 57-99517  6/1982  Japan .

OTHER PUBLICATIONS

Gennaro (1985) Remington's Pharmaceutical Sciences, Merck Publishing, Easton, Pa., pp. 780, 1309, 1314.

*Primary Examiner*—Raj Bawa
*Attorney, Agent, or Firm*—Browdy and Neimark

[57] ABSTRACT

Aloe water containing no aloesin is obtained by forming a pulp from aloe leaves, boiling the pulp at a reduced pressure to obtain vapors, condensing the vapors, and collecting the vapors. The pulp is optionally fermented before boiling. The aloe water can be used for treating skin and hair.

10 Claims, No Drawings

ALOE WATER PREPARATION

This application is a continuation of application Ser. No. 07/601,108, filed Oct. 22, 1990, abandoned.

FIELD OF THE INVENTION

The present Application relates to aloe water, its preparation process, its use, notably in cosmetics and the compositions containing it.

BACKGROUND OF THE INVENTION

Due notably to the constant expansion of out-door leisure activities, skin protection products, indeed skin restorative products are always being sought. These products must be, in addition to being effective, well tolerated, agreeable to use and of a pleasant odour.

Furthermore, products active in combating baldness, either for retarding it, or for encouraging the regrowth of hair, are always being sought.

SUMMARY OF THE INVENTION

The Applicant has discovered with astonishment that aloe water has remarkable properties, as a skin protector and restorer as well as for combating baldness.

The present Application is directed to aloe water, characterized in that it can be obtained by condensation of the vapour from boiling a pulp of aloe leaves. The aloes can be of any known species, and in particular, for example, the species *Aloe barbadensis*. In certain uses, it was discovered that the above aloe water had improved properties when the pulp was subjected to a fermentation before the boiling operation which leads to the condensation of vapour. Accordingly the present Application is also directed to an aloe water described above characterized in that the boiling of the pulp is preceded by a fermentation of said pulp.

Also a subject of the present Application is a preparation process for the above-described aloe water characterized in that a pulp of aloe leaves is subjected to boiling, if desired after fermentation of the pulp and the vapour is condensed to obtain the expected product. The pulp of aloe leaves can be prepared as follows. The aloe leaves, preferably *Aloe barbadensis* are collected, cutting the leaves to a length of about 40 to 50 cm; they are washed and dried, then they are passed through a mill, for example an shredding mill, in order to obtain a homogeneous pulp. The boiling of the pulp takes place preferably in a distiller which is able to be hermetically sealed and containing notably a temperature and pressure indicator. The boiling is preferably carried out under reduced pressure, notably at a pressure of about 1330 Pa (10 mm of mercury). The vapour is then sent, for example, to a condenser made of glass or any other suitable material, cooled, for example, by air and notably by water. The collection of the expected aloe water is preferably carried out in a sterile receptacle.

In the preferred conditions for the implementation of the process described above, the pulp is fermented for a duration of 6 to 48 hours but preferably 24 hours, before the boiling operation.

Also obviously a subject of the invention is the aloe water obtained directly by the implementation of the process described above.

The aloe water described above has remarkable properties both for use in skin treatment and for the treatment of baldness.

The present Application is also directed to cosmetic compositions characterized in that they contain aloe water as defined above.

More particularly a subject of the present invention is cosmetic compositions intended for hair treatment and also those intended for skin treatment. To this end, the aloe water described above can be mixed with liquid preparations or creams, with emulsions, for example, hydrophilic compounds. Also emulsions, notably oil-in-water, can be made starting with the aloe water described above and using suitable surfactants known to one skilled in the art. Also aqueous or alcoholic lotions can be prepared which contain notably an alcohol, particularly a heavy alcohol such as a glycol, glycerol or one of its derivatives.

The aloe water according to the invention can be mixed, if desired, with other active products in order to improve its effectiveness.

The present Application is also directed to a product based on aloe water, characterized in that it contains, besides aloe water, a pulp of the dried solid part of the pulp described above after treatment by boiling, red hibiscus flowers, guava leaves, lemon juice and essence of citronella.

A preferred product according to the invention contains, by weight, in relation to the aloe water, —about 0.005%, for example 0.02 to 0.001 and notably 0.01 to 0.0025% of said pulp of the dried solid part of the aloe leaves pulp after the boiling operation, —about 0.012%, for example, 0.05 to 0.003% and preferably from 0.025 to 0.006% of dehydrated red hibiscus flowers, —about 0.0025%, for example, 0.01 to 0.0006% and notably, from 0.005 to 0.001% of dehydrated guava leaves, —about 0.005%, for example, 0.02 to 0.001% and preferably, from 0.01 to 0.0025% of lemon juice and, —about 0.000015%, for example, from 0.00006 to 0.000003%, preferably 0.00003 to 0.000007% of citronella essence.

A particularly preferred product based on aloe water according to the present invention contains, by weight, 0.12% of dehydrated red hibiscus flowers, 0.0025% of a pulp of the dried solid part of the of aloe leaves pulp, after the boiling operation, 0.0025% of dehydrated guava leaves, 0.005% of lemon juice and 0.000015% of citronella essence relative to the aloe water.

The Hibiscus can be notably *Hibiscus rosa synensis L.*; the guava used is notably *Psidium guajava L.*; the lemon juice is preferably clarified, notably by filtration, and comes from, in particular, *Citrus limon Burmann;* the citronella belongs notably to the species *Cymbopogon citratus* (DC Stapf).

The products described above can be prepared notably by adding, as a decoction, to the aloe water described above, the hibiscus leaves, the guava leaves, the pulp of the solid residue of aloe leaves, the lemon juice, the citronella essence, leaving to steep, separating the liquid from the solid residue and allowing it to ferment, then separating the new solid residue in order to obtain the expected product in a liquid form, and adding, if desired, the additive or additives.

The red hibiscus flowers employed are preferably washed and dehydrated.

The guava leaves are notably washed, dehydrated and ground.

The lemon juice can be used as it is but is advantageously clarified, notably by filtration.

When the various constituents are brought together, the whole is left to steep in a vat, preferably for about 72 hours, when the operation takes place at ambient temperature. This duration can be shortened by using gentle heating.

The subsequent separation of the residues can be carried out according to well-known techniques, such as centrifuging, and notably filtration.

The liquid thus collected is then fermented for about 4 months, notably from 3 to 5 months, according to the quality and quantity of the elements employed. When the content of hibiscus tannins is significant, a longer fermentation time is preferred.

The subsequent separation can also be carried out as indicated above, notably by filtration.

The product thus obtained can be used as it is but it is possible to add additives to it such as anti-oxidants, such as ascorbic acid, for example at the rate of 30 mg/liter, anti-bacterial agents, such as Dalibour water, at the rate, in this case, of 3 ml/liter, or other preservatives.

The above products intended for cutaneous use can be mixed with sun-tanning liquid or cream preparations, or to an emulsion, for example hydrophilic. There can also be made, starting with such products and using suitable surfactants well-known to one skilled in the art, oil-in-water emulsions.

Lotions which contain notably an alcohol, particularly a heavy alcohol, such as glycol, glycerol or one of its derivatives, can also be prepared It is understood that it is possible to add, according to requirements, other additives such as perfumes, preferably hypoallergenic, colourants or filters, notably sun filters.

The products according to the present invention have remarkable properties; notably they allow the moisturizing of the skin, are soothing, softening, anti-inflammatory; used as preventatives, they avoid the formation of blisters despite prolonged exposure to the sun; furthermore they allow a longer exposure time to the sun, notably for sensitive types of skin, for example the white skin of blonde or red-headed people, as well as sensitive skin in general, particularly the skin of babies.

The products according to the present invention can be used as a preventative treatment vis-a-vis the sun and wind, due notably to their moisturizing action which avoids the skin drying out and also as a curative treatment, for example after prolonged exposure to the sun.

The products according to the present invention also possess remarkable healing properties.

The products according to the present invention allow moreover the almost instantaneous calming of the painful effects of sun burn and, used rapidly, severely restrict the appearance of blisters on the skin.

The products of the invention are not greasy and, due to this; fact, allows one to dress immediately after their application. They also present the advantage, due to their fluidity, of being able to be packaged in a spray, in an atomizer or in a microniser, thus avoiding a painful application, given that a massage is not necessary for their penetration. In effect, the products described above are easily absorbed by the epidermis.

Equally a subject of the present Application is a product based on aloe water characterized in that it contains, in addition to aloe water, camphor, copper sulphate and triethanolamine.

In the preferred conditions, the product described above contains, by weight, relative to the aloe water, about 0.05% of camphor, for example 0.2 to 0.01%, and notably 0.2 to 0.025%, about 0.005% of copper sulphate, for example 0.01 to 0.0006% and notably 0.006 to 0.001% of said copper sulphate, about 0.2% of triethanolamine, for example 0.5 to 0.01% and notably 0.3 to 0.1% and about 0.1% of lactic acid, for example 0.5 to 0.01% and notably 0.3 to 0.05%.

The copper sulphate is advantageously used in the form of its pentahydrate. Also other non-toxic divalent copper salts can be used.

A preferred product according to the invention contains moreover lactic acid. A quite particularly preferred product according to the invention has the following composition, given for one liter of aloe water according to the present invention:

0.05% of camphor, 375 mg/l of copper sulphate pentahydrate, 0.3% of ethanol, 0.238% of triethanolamine, 0.0952% of lactic acid. The pH of the composition is established at 7.5.

The product described above finds remarkable uses in the treatment of baldness. In effect, it is capable of reducing seborrhoea, of reactivating the hair cells and stopping hair loss. Also, a stimulation of the growth of keratinocytes and hair growth is noticed in the majority of cases. Also a change in the nature of the hair, it becoming thicker, was noticed.

The product described above can be used as follows: the operation is carried out with two applications per day, for example morning and evening, notably on clean, dry hair. The applications can be carried out section by section on the hair roots, from the top of the skull and massaging the scalp to allow the product to penetrate. It is also desirable that the hair is not rinsed after application.

The products described above are remarkably well tolerated. In fact, no irritation, intolerance or sensitisation reaction has been observed during the various clinical trials, even those of long duration. The properties of the products of the present Application are illustrated hereafter in the experimental part.

The following examples illustrate the present invention without however limiting it.

EXAMPLE 1

Leaves of *Aloe bardadensis* are collected by cutting the leaves to a length of about 40 to 50 cm, they are washed, dried and broken up in a shredding mill in order to obtain a homogeneous pulp, which is then fermented for 24 hours. After fermentation, the whole is placed in a hermetically sealed distiller, with a capacity of 150 liters, having temperature and pressure indicators and an outlet of 3 cm diameter to collect the vapour. The vapour is sent to a water-cooled glass condenser. The operation takes place at ebullition, under reduced pressure, at 10 mm of mercury. The expected product is obtained with a yield of about 65%. The output of the preparation is about 4 liters per hour. The implementation of 150 kg of aloe leaves therefore produces 97 liters of aloe water according to the invention in 24 hours, called hereafter P2. The solid pulp is collected, dried and broken up to obtain a product which is hereafter called P3.

The juice (P2) is colourless, translucent and has a density of 0.998.

An aloe water P2 was also prepared by milling the leaves. The solid part of the dried and milled pulp is called P3.

Furthermore, the red flowers of *Hibiscus rosa sinensis L* are washed and dehydrated, the leaves of *Psidium*

*guajava* are dehydrated and broken up. 30 liters of P2 are placed in a vat and 0.012% of hibiscus flowers, 0.0025% of guava leaves, 0.005% of P3, 0.005% of filtered lemon juice and 0.000015% of citronella essence are added as a decoction at about 20° C.

A similar preparation is made starting with P'2 and P'3. The whole is left for 72 hours at about 20° C., the decoction is filtered, the filtrate is placed in a fermenter for 100 days at about 30° C. under a pressure of 150 mm water gauge and filtered in order to obtain the desired products, of a brown-red translucent appearance, a slightly fruity and acidic odour and of pH 5.5.

EXAMPLE 2

3 ml of Dalibour water and 30 mg of ascorbic acid are added to one liter of products obtained in Example 1 in order to obtain long-life preparations.

EXAMPLE 3

Dermatological Milk dermatological milks were prepared having the following composition per bottle:
—products of Example 1: 70 ml
—glycerol stearate; polyoxyethylene ketostearate; stearyl isononanoate; glycerol; lactic acid; triethanolamine: 30 ml

EXAMPLE 4

Non-alcoholic Lotion 200 ml of products of Example 1 are packaged in 200 ml aerosol bottles.

EXAMPLE 5

Cream

Creams were prepared containing the following:
—products of Example 1: 70 ml
—glycerol stearate; polyoxyethylene ketostearate; di-n-butyl-adipate; paraffin oil; glycerol; lactic acid; triethanolamine: 30 ml

EXAMPLE 6

Gel

Gels were prepared corresponding to the following formula:
—products of Example 1: 50 ml
—monopropyleneglycol; cross-linked polyacrylic acid; lactic acid; triethanolamine: 50 ml

EXAMPLE 7

Effectiveness Test of the Products of Example 1

A) A third degree burn spread over an area of 12 cm$^2$ was treated. The products of Example 2 were applied directly to the burn. The application was repeated every two hours, without covering the burn. The next day, three further applications were made.

30 minutes after the first application, almost total relief from pain was observed. The day after this first application, the burn was covered with a thin clean scab, without any apparent weeping or infection.

On days 3, 4 and 5 two applications per day were carried out using a sterile compress. After three weeks, the skin was clean and smooth, without scars or blisters.

B) The products of Example 1 were used on ten subjects suffering from first degree burns after prolonged exposure to ultra-violet light. The majority showed pain on being touched and difficulty in moving the limbs concerned without feeling a sharp pain, taking into account the severity of the sunburn.

The skin was of several types, notably of red-headed subjects.

Two hours after the end of exposure, the test product was applied. An immediate easing of the pain, the return of non-painful movement, also a sensation of freshness was noticed. Touching or rubbing the burn was also not painful.

It was also observed that the suntan obtained by exposure to ultra-violet light was retained longer in subjects who had benefited from a treatment with the product of the present invention, relative to the subjects who had not benefited from it.

The products prepared starting with P2 and P3 showed themselves to be more active than those prepared starting with P'2 and P'3.

EXAMPLE 8

Hair Lotion a) Preparation of copper sulphate 29 g of 99% pure copper sulphate pentahydrate is dissolved in 230 ml of distilled water at 25° C. which corresponds to a content of copper sulphate of 12.6% relative to the liquid.

b) Preparation of triethanolamine and lactic acid 175 ml of triethanolamine and 70 ml of lactic acid are dissolved in 524 ml of distilled water.

c) Preparation of an aqueous lotion intended to treat baldness.

97 liters of aloe water (P2) is mixed with 230 ml of the above preparation of copper sulphate, 524 ml of the above preparation of triethanolamine-lactic acid and 1.5 liters of camphorated alcohol in order to obtain the expected product.

The product of Example 8 reactivates hair cells and stops hair loss.

I claim:

1. Aloe water containing no aloesin obtained by a process consisting of the following steps:
   forming a pulp from aloe leaves;
   boiling said pulp at a pressure of about 10 mm of mercury to obtain vapors;
   condensing said vapors; and
   collecting said vapors.

2. A method for preparing aloe water containing no aloesin consisting of the following steps:
   forming a pulp from aloe leaves;
   boiling said pulp at a pressure of about 10 mm of mercury to obtain vapors;
   condensing said vapors; and
   collecting said vapors.

3. The aloe water of claim 1 wherein said aloe leaves are of the species *Aloe barbadensis*.

4. The method of claim 2 wherein said aloe leaves are of the species *Aloe barbadensis*.

5. A cosmetic composition consisting essentially of a cosmetically effective amount of aloe water prepared according to the method of claim 2 and a cosmetically acceptable carrier.

6. A cosmetic composition consisting essentially of a cosmetically effective amount of aloe water prepared according to the method of claim 2, camphor, copper sulfate, triethanolamine, and lactic acid, and a cosmetically acceptable carrier.

7. A method for reactivating hair cells and reducing hair loss comprising applying to the head an effective amount of aloe water prepared according to the method of claim 2.

8. The aloe water of claim 1 wherein said pulp is fermented prior to boiling for a period of from 6 to 48 hours.

9. The aloe water of claim 1 wherein said pulp is fermented prior to boiling for a period of from 6 to 48 hours.

10. The method of claim 2 wherein said pulp is fermented prior to boiling for a period of from 6 to 48 hours.

* * * * *